United States Patent
Leszczuk (10) Patent No.: US 11,705,241 B2
(45) Date of Patent: *Jul. 18, 2023

(54) AGGREGATOR SYSTEM FOR ENABLING ONLINE ACCESS TO ENCOUNTER DATA FROM MULTIPLE DISPARATE SOURCES

(71) Applicant: Zocdoc, Inc., New York, NY (US)

(72) Inventor: William M. Leszczuk, Scotch Plains, NJ (US)

(73) Assignee: Zocdoc, Inc., New York, NY (US)

( * ) Notice: Subject to any disclaimer, the term of this patent is extended or adjusted under 35 U.S.C. 154(b) by 112 days.

This patent is subject to a terminal disclaimer.

(21) Appl. No.: 17/338,275

(22) Filed: Jun. 3, 2021

(65) Prior Publication Data

US 2021/0295986 A1 Sep. 23, 2021

Related U.S. Application Data

(63) Continuation of application No. 15/222,094, filed on Jul. 28, 2016, now Pat. No. 11,056,230.

(51) Int. Cl.
*G16H 40/20* (2018.01)
*G16H 10/60* (2018.01)

(52) U.S. Cl.
CPC .............. *G16H 40/20* (2018.01); *G16H 10/60* (2018.01)

(58) Field of Classification Search
USPC .......................................................... 705/3
See application file for complete search history.

(56) References Cited

U.S. PATENT DOCUMENTS 8,938,421 B2 * 1/2015 Jain .................... G06F 13/22
707/674
2004/0019501 A1 * 1/2004 White ................... G16H 15/00
705/2

FOREIGN PATENT DOCUMENTS

WO WO-2016196023 A1 * 12/2016 ........... G06F 19/322

OTHER PUBLICATIONS

Haras, Consuela, Patient Data Synchronization Process in Continuity of Care Environment, AMIA Annu Symp Proc. 2005; 2005: 296-300 (Year: 2005).*

* cited by examiner

*Primary Examiner* — Michael Young
(74) *Attorney, Agent, or Firm* — White and Williams LLP (57) ABSTRACT

Disclosed are systems, methods, and non-transitory computer-readable enabling online access to encounter data across multiple disparate sources. The method includes providing a synchronizer application configured to access data of a practice group server, receiving, by an aggregator server, a start time and a duration of a healthcare appointment, and determining a completion time of the healthcare appointment. Based on the completion time, the aggregator server transmits a request for encounter data for the healthcare appointment to the synchronizer application and then receives and stores the encounter data in an aggregator database. The aggregator server generates an electronic alert addressed to a computing device accessible by the patient and transmits the alert to the computing device. The aggregator server receives an electronic response to the alert and provides an interactive user interface to the computing device configured to display the encounter data on the computing device.

18 Claims, 5 Drawing Sheets

AGGREGATOR SYSTEM FOR ENABLING ONLINE ACCESS TO ENCOUNTER DATA FROM MULTIPLE DISPARATE SOURCES

This application is a continuation of U.S. patent application Ser. No. 15/222,094, filed Jul. 28, 2016, now U.S. patent Ser. No. 11/056,230, the contents of which is hereby incorporated by reference in its entirety.

TECHNICAL FIELD

The present disclosure pertains to aggregating encounter data, and more particularly to systems and methods for aggregating and enabling online access to encounter data across multiple disparate sources.

BACKGROUND

The process for obtaining claim information in current healthcare systems is slow, complicated, and lacks transparency. A patient must often wait weeks or months after an office encounter for a claim to be resolved before receiving an Explanation of Benefits (EOB), and even then the patient is often left with inaccurate information regarding what procedures and tests were ordered, which were performed, for which the patient and/or insurer were billed, and whether or not any or all of the procedures and tests were necessary.

Moreover, translations between proprietary software workflows, taxonomies, and medical codes during the claims process obscure the link between the office encounter and the claim, making it technically difficult, if not impossible, to access meaningful encounter data prior to generation of the EOB. This ultimately requires the patient to wait for receipt of the EOB before deciphering and correcting problems in billing data for each provider, insurer, and encounter without any centralized or timely way of doing so. Accordingly, there is a need for a system capable of overcoming the technical difficulties associated with accessing encounter data prior to generation of the EOB and matching the encounter data to a specific office encounter.

SUMMARY

Embodiments of the invention concern systems, methods, and non-transitory computer-readable media for enabling online access to encounter data from multiple disparate sources. In doing so, the present disclosure alleviates the delay, fragmentation, and lack of transparency issues in past claims processing systems by revealing encounter data to the patient in an online, near-real-time manner. Moreover, the presently disclosed systems, methods, and non-transitory computer-readable media overcome technical difficulties in accessing encounter data prior to generation of the EOB and matching the encounter data to a specific office encounter by cutting out intermediary systems, protocols, taxonomy translations, and offline processes utilized in past claims processing systems.

In a first embodiment of the invention a method includes providing a synchronizer application configured to access data associated with a practice group server, receiving, by an aggregator server, a start time and a duration of a healthcare appointment between a patient and a physician associated with the practice group server, determining, by the aggregator server, a completion time of the healthcare appointment based at least in part on the start time and the duration, based on the completion time, transmitting, by the aggregator server and to the synchronizer application, a request for encounter data for the healthcare appointment, wherein the synchronizer application is configured to poll the practice group server to retrieve the encounter data in response to the request, receiving, by the aggregator server and from the synchronizer application, the encounter data, wherein the encounter data includes one or more services rendered during the healthcare appointment, storing, by the aggregator server, the encounter data in an aggregator database, generating, by the aggregator server, an electronic alert addressed to a computing device accessible by the patient, the alert indicating an availability of encounter data for the healthcare appointment, transmitting, by the aggregator server, the alert to the computing device, receiving, by the aggregator server and from the computing device, an electronic response to the alert, wherein the response includes a request to access the encounter data for the healthcare appointment, and providing, by the aggregator server, an interactive user interface to the computing device, wherein the interactive user interface is configured to display the encounter data on the computing device.

In one embodiment, the request includes identifying information for the healthcare appointment, and wherein synchronizer application is further configured to match the healthcare appointment to the encounter data based on the request.

In one embodiment, at least a portion of the encounter data is encoded, and wherein the aggregator server is configured to decode and normalize the encounter data prior to storing in the aggregator database.

In one embodiment, the encounter data is encoded using Current Procedural Terminology (CPT) codes.

In one embodiment, the alert is one or more of an email, a Short Message Service (SMS), a Multimedia Messaging Service (MMS), a push notification, or an application launch.

In one embodiment, the method further includes detecting, by the aggregator server, a delay or a rescheduling of the healthcare appointment, and recalculating, by the aggregator server, the completion time of the healthcare appointment based at least in part on the delay or the rescheduling.

In one embodiment, the method further includes receiving, by the aggregator server, a booking request submitted via the interactive user interface, the booking request including at least an appointment time for a second healthcare appointment, and booking, by the aggregator server, the second healthcare appointment.

In one embodiment, the method further includes receiving, by the aggregator server, a dispute message submitted via the interactive user interface, the dispute message identifying at least a portion of the encounter data being disputed, and transmitting, by the aggregator server and to the practice group server, the dispute message.

In one embodiment, the method further includes identifying, by the aggregator server, a healthcare expenditure based at least in part on the encounter data, and categorizing, by the aggregator server, the healthcare expenditure as an out-of-pocket expenditure or a medical account eligible expenditure.

In a second embodiment a system includes a practice group server, and an aggregator server configured to provide a synchronizer application configured to access data associated with the practice group server, receive a start time and a duration of a healthcare appointment between a patient and a physician associated with the practice group server, determine a completion time of the healthcare appointment based at least in part on the start time and the duration, based on the completion time, transmit, to the synchronizer application, a request for encounter data for the healthcare appointment, wherein the synchronizer application is configured to poll the practice group server to retrieve the encounter data in response to the request, receive, from the synchronizer application, the encounter data, wherein the encounter data includes one or more services rendered during the healthcare appointment, store the encounter data in an aggregator database, generate an electronic alert addressed to a computing device accessible by the patient, the alert indicating an availability of encounter data for the healthcare appointment, transmit the alert to the computing device, receive, from the computing device, an electronic response to the alert, wherein the response includes a request to access the encounter data for the healthcare appointment, and provide an interactive user interface to the computing device, wherein the interactive user interface is configured to display the encounter data on the computing device.

In one embodiment, the request includes identifying information for the healthcare appointment, and wherein synchronizer application is further configured to match the healthcare appointment to the encounter data based on the request.

In one embodiment, the aggregator server is further configured to receive a dispute message submitted via the interactive user interface, the dispute message identifying at least a portion of the encounter data being disputed and transmit, to the practice group server, the dispute message.

In one embodiment, the alert is one or more of an email, a Short Message Service (SMS), a Multimedia Messaging Service (MMS), a push notification, or an application launch.

In one embodiment, the synchronizer application is configured to continuously poll the practice group server until the encounter data is retrieved or until a predetermined timeout occurs.

In one embodiment, the interactive user interface includes encounter data for one or more prior healthcare appointments by the patient.

In a third embodiment a non-transitory computer-readable storage medium having stored therein instructions which, when executed by a processor, cause the processor to perform operations including providing a synchronizer application configured to access data associated with a practice group server, receiving, by an aggregator server, a start time and a duration of a healthcare appointment between a patient and a physician associated with the practice group server, determining, by the aggregator server, a completion time of the healthcare appointment based at least in part on the start time and the duration, based on the completion time, transmitting, by the aggregator server and to the synchronizer application, a request for encounter data for the healthcare appointment, wherein the synchronizer application is configured to poll the practice group server to retrieve the encounter data in response to the request, receiving, by the aggregator server and from the synchronizer application, the encounter data, wherein the encounter data includes one or more services rendered during the healthcare appointment, storing, by the aggregator server, the encounter data in an aggregator database, generating, by the aggregator server, an electronic alert addressed to a computing device accessible by the patient, the alert indicating an availability of encounter data for the healthcare appointment, transmitting, by the aggregator server, the alert to the computing device, receiving, by the aggregator server and from the computing device, an electronic response to the alert, wherein the response includes a request to access the encounter data for the healthcare appointment, and providing, by the aggregator server, an interactive user interface to the computing device, wherein the interactive user interface is configured to display the encounter data on the computing device.

In one embodiment, the request includes identifying information for the healthcare appointment, and wherein synchronizer application is further configured to match the healthcare appointment to the encounter data based on the request.

In one embodiment, at least a portion of the encounter data is encoded, and wherein the aggregator server is configured to decode and normalize the encounter data prior to storing in the aggregator database.

In one embodiment, the synchronizer application is configured to continuously poll the practice group server until the encounter data is retrieved or until a predetermined timeout occurs.

In one embodiment, the non-transitory computer-readable medium has further instructions which cause the processor to perform operations including receiving, by the aggregator server, a dispute message submitted via the interactive user interface, the dispute message identifying at least a portion of the encounter data being disputed, and transmitting, by the aggregator server and to the practice group server, the dispute message.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

As used herein, the terms "component", "system", or "module" are intended to refer to a computer-related entity, either hardware, software, a combination of hardware and software, or software in execution. For example, a component may be, but is not limited to, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed between two or more computers.

As used herein, the term "provider" includes a physician, doctor or other medical professional (e.g., a nurse, physician assistant, etc.) administering patient care, as well as members of his or her staff that assist in providing such care or are responsible for maintaining the provider's scheduling calendar, patient records, billing, insurance, prescription, and other services.

As used herein, the terms "practice group" or "provider group" may be any entity linking a group of providers through shared facilities, services or referral agreements. This may include, but should not be limited to, one or more hospitals, clinics, pharmacies, insurance networks, medical groups, and multi-doctor practices.

A "user" of the system described herein may be a patient or an entity acting on behalf of the patient. A "patient" as used herein means an existing patient or a prospective patient of a provider or practice group.

As used herein, "communicatively coupled" is taken to mean any data transmission link between two or more computing devices or components, wired or wireless. Examples of such data transmission links include, but are not limited to, a Local Area Network (LAN), a Wide Area Network (WAN), Intranet, Internet, or any other wired or wireless networking and data transmission technologies that are known in the art.

Figure 1:
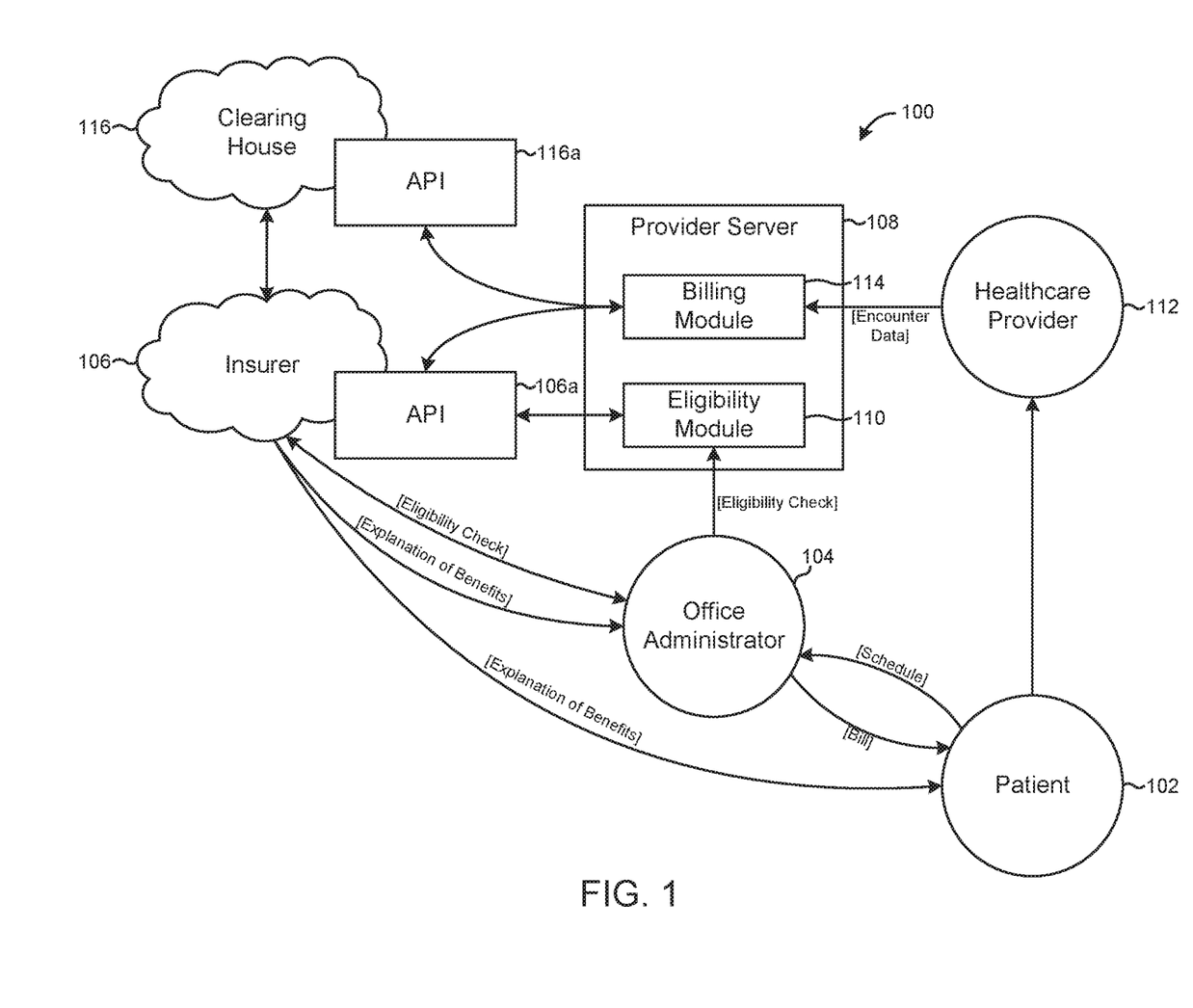
FIG. 1 illustrates a schematic diagram of an exemplary claims process in a current healthcare system.

Having discussed some basic terminology as used herein, the disclosure now turns to FIG. 1. FIG. 1 illustrates a schematic diagram of a typical claims process in a current healthcare system 100 without the benefit of the present invention. The process begins with a patient 102 calling a provider group administrator 104 to schedule an office appointment and provide insurance information. Based on the insurance information, administrator 104 performs an eligibility check with an insurer 106 via phone, fax, or a call to insurer API 106a through an eligibility module 110 on provider server 108. Once the eligibility check is complete, administrator 104 schedules an office appointment between patient 102 and a healthcare provider 112.

After or during the scheduled office encounter between patient 102 and provider 112, provider 112 enters encounter data into a billing module 114 on provider server 108. The encounter data may include a description or indication of the healthcare services provided and/or ordered, the categories of such healthcare services, medical code numbers (such as Current Procedural Terminology (CPT) codes), evaluation and management data (may be referred to as evaluation/management coding), the disposition of the patient visit (e.g., sick visit, well visit), diagnostics to be performed, cost data, and/or similar information. Once entered, the encounter data is transmitted from billing module 114 on provider server 108 to insurer 106 (e.g., via API 106a) and/or clearing house 116 (e.g., via API 116a) for resolution. Insurer 106, clearing house 116, and provider server 108 resolve the claim, and insurer 106 sends a paper Explanation of Benefits (EOB) (i.e., a statement explaining what healthcare treatments and/or services described in the encounter data were paid for on behalf of patient 102) to administrator 104 and patient 102. Finally, administrator 104 sends a paper bill to patient 102 for the remainder of the negotiated cost of services not reimbursed by insurer 106.

As illustrated in FIG. 1, the process for obtaining claim information in current healthcare system 100 is slow, complicated, and lacks transparency. Indeed, a patient must wait weeks or months after an office encounter for a claim to be resolved before receiving an EOB, and even then the patient is often left with inaccurate information regarding what procedures and tests were ordered, which were performed, for which the patient and/or insurer were billed, and whether or not any or all of the procedures and tests were necessary. Moreover, the lack of synchronization between parties involved in the claims process, such as the insurer and the office administrator, can cause a long delay between receipt of the EOB and the bill which further confuses and burdens the patient. This ultimately leaves the patient to decipher and correct problems in billing data for each provider, insurer, and encounter without any centralized or timely way of doing so.

Accordingly, systems, methods, and non-transitory computer-readable media are described herein for enabling online access to encounter data across multiple disparate sources on a centralized service provider (aggregator) system. In doing so, the present disclosure alleviates the non-transparency, delay, and fragmentation issues in past claims processing systems by revealing encounter data to the patient in an online, near-real-time manner. This allows encounter data to be reviewed and corrected before a healthcare claim is processed, before an EOB is generated, and before a bill is received. The present disclosure not only improves upon the efficiency of past processes, but overcomes technical difficulties in accessing encounter data prior to generation of the EOB and matching the encounter data to a specific office encounter by cutting out intermediary systems, protocols, taxonomy translations, and offline processes utilized in past claims processing systems.

Figure 2:
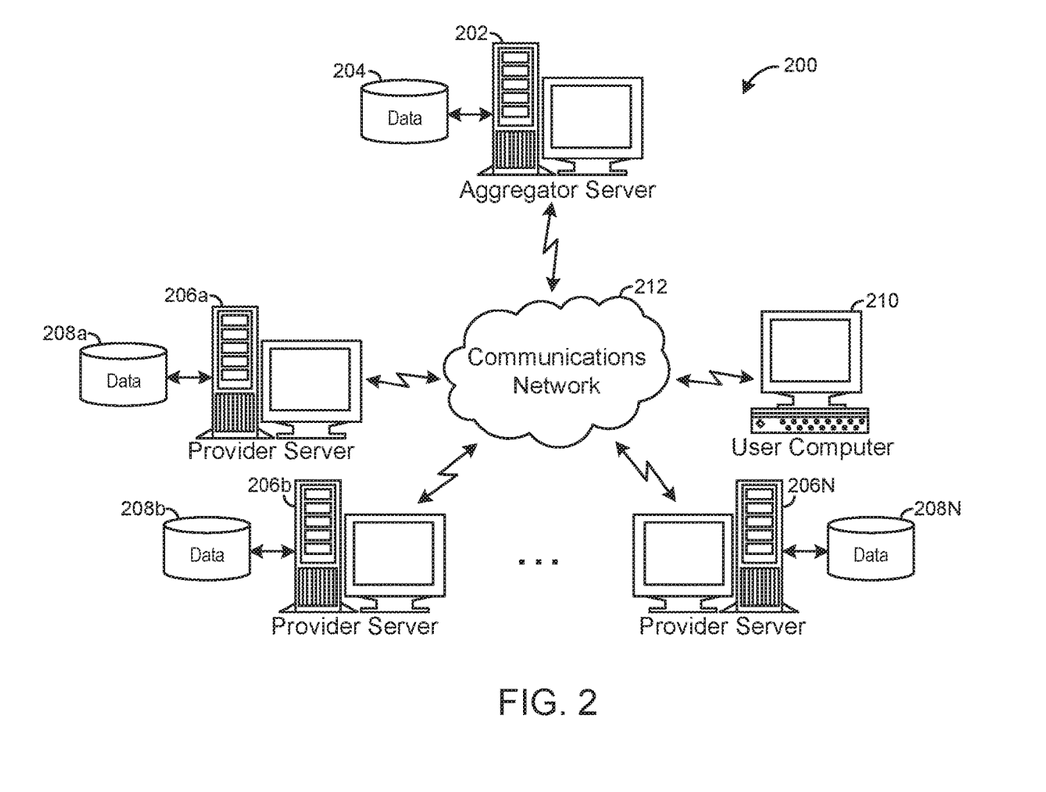
FIG. 2 illustrates a schematic diagram of an exemplary communications network for implementing various embodiments of the present disclosure.

The disclosed system and method are best understood in the context of the environment in which they operate. Accordingly, FIG. 2 illustrates a schematic diagram of a system 200 for enabling online access to encounter data including an aggregator server 202 in network communications with various disparate and unaffiliated sources, such as provider group servers 206a, 206b, . . . , 206N and user computer 210. Each of the components is communicatively coupled via a network 212 (e.g., the Internet) to enable communications between one another using communication protocols, such as TCP/IP. Moreover, each component may have an attached data storage system, such as data storage systems 204, 208a, 208b, ..., 208N, for storing software applications and data.

Aggregator server 202 may be provided on a single computer server or multiple computer servers that are communicatively coupled via one or more networks. The one or more computer servers may be housed in a single location or distributed over a plurality of different geographic locations and regions. In some embodiments, aggregator server 202 may be provided by one or more cloud computing clusters. Similarly, each of provider group servers 206a, ..., 206N may be provided on one or more dedicated servers or cloud computing clusters housed in a single location or operating in a distributed environment. User computer 210 may be any computing device including, but not limited to, a desktop computer, a laptop computer, a mobile computing device, and the like. Suitable hardware for implementing each of aggregator server 202, provider group servers 206a, ..., 206N, and user computer 210 are discussed in detail with reference to FIG. 5.

In accordance with one embodiment, aggregator server 202 can provide a network-based service and interface to each of provider group servers 206a, 206b, ..., 206N and user computer 210. For example, aggregator server 202 can communicate (e.g., via network 212) with each of provider group servers 206a, 206b, ..., 206N to aggregate data, such as healthcare encounter data, healthcare appointment availability data, and/or other healthcare data, from the provider servers. In some cases, aggregator server 202 can install a synchronizer application on each of provider group servers 206a, 206b, ..., 206N, and the synchronizer application can retrieve the data from the respective provider group server and transmit the data to aggregator server 202 via network 212. In other cases, aggregator server 202 can ingest the data via web crawlers, application programming interfaces (APIs), or other communications over network 212. Once received, aggregator server 202 can process and store the aggregated data in storage system 204 and, based on the data, provide the network-based service and interface to each of provider group servers 206a, 206b, ..., 206N and user computer 210.

Figure 3:
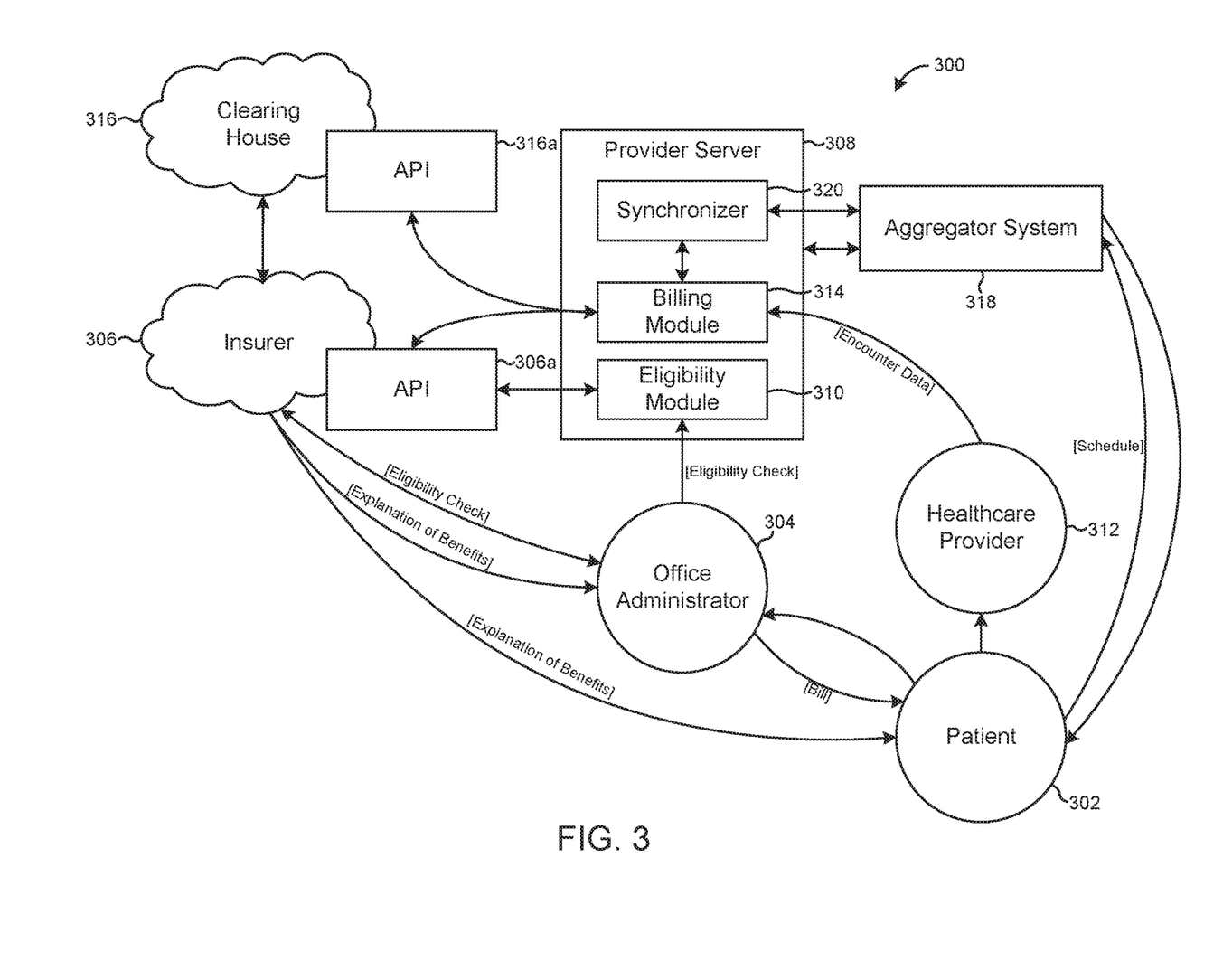
FIG. 3 illustrates a schematic diagram of an exemplary system for enabling access to encounter data across multiple disparate sources in accordance with the present disclosure.

FIG. 3 illustrates a schematic diagram of a system 300 for enabling online access to encounter data from multiple disparate sources. System 300 begins with a patient 302 booking an available healthcare appointment via an online interface provided by aggregator system 318. Various systems and methods for facilitating online booking of healthcare appointments across multiple disparate providers are described in the following commonly owned (and herein incorporated by reference in their entirety) US patent applications:

U.S. Ser. No. 12/210,664 filed 15 Sep. 2008 entitled CENTRALIZED MARKETPLACE FOR HEALTHCARE APPOINTMENTS ACROSS PRACTICE GROUPS (US 2010/0070295);

U.S. Ser. No. 13/344,966 filed 3 May 2012 entitled CONSUMER PORTAL FOR HEALTHCARE APPOINTMENTS ACROSS PRACTICE GROUPS (US 2012/0109679);

U.S. Ser. No. 12/210,765 filed 15 Sep. 2008 entitled DATA SYNCHRONIZATION FOR BOOKING OF HEALTHCARE APPOINTMENTS ACROSS PRACTICE GROUPS (US 2010/0070297); and U.S. Ser. No. 13/796,417 filed 12 Mar. 2013 entitled METHOD AND APPARATUS FOR GUIDING PATIENTS TOWARD HEALTHCARE GOALS (US 2014/0278449).

By way of example, to facilitate online booking of healthcare appointments aggregator system 318 can maintain a centralized database of available appointment times and other relevant information across multiple disparate provider groups. For instance, aggregator system 318 can install software (e.g., synchronizer application 320) on each provider group server (e.g., provider group server 308) which automatically extracts available appointment times at regular intervals. Patient 302 can then access the online interface provided by aggregator system 318 and can create a secure user account to search for and select an available healthcare appointment for booking. After an available office appointment is selected by patient 302, aggregator system 318 can confirm the appointment with the respective provider group as a booked appointment.

However, it should be noted that system 300 can enable online access to encounter data for appointments booked through means other than aggregator server 318 as described below; for example, system 300 can be enabled to process appointments booked by a patient 302 directly with healthcare provider 312 or office administrator 304, or through automated systems acting on behalf of or otherwise provided by healthcare provider 213 or office administrator 304.

At the time of the scheduled office appointment, patient 302 can provide his or her insurance information to provider group administrator 304. Based on the insurance information, administrator 304 can perform an eligibility check with an insurer 306 via phone, fax, or a call to insurer API 306a through an eligibility module 310 on provider server 308. Alternatively or in addition, patient 302 can provide the insurance information to aggregator system 318 during the initial booking of the appointment, and aggregator system 318 and/or administrator 304 can perform the eligibility check with insurer 306 through one of the means illustrated above.

During or shortly after the scheduled office encounter between patient 302 and provider 312, provider 312 or a representative thereof enters encounter data into a billing module 314 on provider server 308. Billing module 314 can be any interface into which encounter data is entered and then forwarded to insurer 306 and/or clearing house 316 via network-based communications, fax, phone, or the like. Billing module 314 can also include a database for storing the encounter data. Once entered, the encounter data is transmitted from billing module 314 on provider server 308 to insurer 306 (e.g., via API 306a) and/or clearing house 316 (e.g., via API 316a) for resolution. Insurer 306, clearing house 316, and provider server 308 resolve the claim, and insurer 306 sends a paper EOB to administrator 304 and patient 302. Finally, administrator 304 sends a paper bill to patient 302 for the remainder of the negotiated cost of services not reimbursed by insurer 306.

However, as discussed above with reference to FIG. 1, the process of communicating encounter data and resolving a claim between provider server 308, insurer 306, and clearing house 316 is slow, complicated, and lacks transparency. This ultimately requires patient 302 to wait weeks or longer before receiving an EOB, and even then the patient must decipher and correct problems in billing data for each provider, insurer, and encounter without any centralized or timely way of doing so. Moreover, the current healthcare system paradigm of mapping encounter data from a provider server's proprietary taxonomies and software workflows to medical code numbers (e.g., CPT codes, X12 codes, etc.) results in a loss of information that obscures the connection between a claim in insurer 306 or clearing house 316 and the corresponding office encounter between patient 302 and provider 312. This makes it technically difficult, if not impossible, to tap into insurer 306 (e.g., via API 306*a*) or clearing house 316 (e.g., via API 316*a*) to access encounter data for a given patient before generation of the EOB, as the claim information in insurer 306 or clearing house 316 lacks the information necessary to match with a specific office encounter.

Accordingly, aggregator system 318 can provide a synchronizer application 320 configured to selectively retrieve data, such as encounter data, from provider server 308 and its associated applications (e.g., billing module 314). For instance, in some cases, aggregator system 318 can extend a previously installed synchronizer application 320 to retrieve the encounter data. In other cases, aggregator system 318 can install or otherwise provide a synchronizer application 320 configured to retrieve the encounter data in addition to any existing synchronizer infrastructure.

Aggregator system 318 can then detect a completion time of the office encounter between patient 302 and provider 312. For example, in cases where patient 302 scheduled the office appointment via aggregator system 318, aggregator system 318 can calculate the completion time based on a known appointment start time and a known appointment duration. On the other hand, in cases where patient 302 scheduled the office appointment through means other than aggregator server 318, the practice group could direct or otherwise enable aggregator system 318 to retrieve the appointment start time and appointment duration from provider server 308 to calculate the appointment completion time. Aggregator system 318 can also detect a delay or a rescheduling of the appointment, and can recalculate the appointment completion time based on the delay or rescheduling.

After detecting the completion of the office encounter, aggregator system 318 can transmit a request for encounter data to synchronizer 320. The request can include information such as a patient name, a provider name, an appointment time, a patient ID, insurance information, and/or other identifying healthcare information which enables synchronizer 320 to identify and match the office appointment to the corresponding encounter data. In response to the request, synchronizer 320 begins polling certain data fields in billing module 314 (or its associated database) to retrieve the encounter data. In other cases, synchronizer 320 can detect the completion time of the office encounter and can automatically begin polling billing module 314 to retrieve the encounter data. Synchronizer 320 can continue polling billing module 314 until the encounter data is retrieved or until a predetermined timeout occurs. Once synchronizer 320 obtains the encounter data, it transmits the encounter data to aggregator system 318 where it is associated with the user account of patient 302 and stored in an aggregator database. In some cases, some or all of the encounter data is encoded using medical code numbers (e.g., CPT codes, X12 codes, etc.) or other proprietary codes. In such cases, aggregator system 318 or synchronizer 320 can decode and normalize the encounter data prior to storage in the aggregator database.

After the encounter data is received and stored, aggregator system 318 can generate an electronic alert and can transmit the alert to a computing device accessible by patient 302 via one or more of an email, a Short Message Service (SMS), a Multimedia Messaging Service (MMS), a push notification for a software application, or the like. The alert can include the encounter data, a redacted version of the encounter data, and/or an indication that the encounter data is available in aggregator system 318 for the office appointment between patient 302 and provider 312. Moreover, the alert can include in interactive link which, when selected by patient 302, generates and transmits an electronic response to aggregator system 318 requesting access to the encounter data. In some cases, the response can include credentials (e.g., a username and password, a pin code, biometric credentials, etc.) provided by patient 302 to access their secure user account with aggregator system 319. Once the electronic response is received, aggregator system 318 can provide an interactive graphical user interface (GUI) to the computing device, for example, via an online portal, a software application, or the like. The interactive GUI causes the computing device to display the encounter data, enabling patient 302 to securely access and review, in at least near real-time, the encounter data which was or will be submitted to insurer 306 and/or clearing house 316 for processing. The interactive GUI can also display encounter data associated with prior office encounters in an aggregated fashion.

Using the interactive GUI, patient 302 can check the data for accuracy, view negotiated prices for procedures, ensure unnecessary claims are not being submitted, and the like. The interactive GUI can also enable patient 302 to dispute encounter data by submitting an electronic dispute message to one or more of provider server 308, insurer 306, or clearing house 316 via aggregator system 318. Furthermore, the interactive GUI can allow patient 302 to book a follow-up healthcare appointment via aggregator system 318.

Aggregator system 318 can also process the encounter data to provide additional features and services to patient 302 and other entities. For example, aggregator system 318 can process the encounter data to identify one or more trends in healthcare expenditures by patient 302. Based on the identified trends, aggregator system 318 can provide recommendations to patient 302, for example, by displaying the recommendations on the interactive GUI. In some embodiments, aggregator system 318 can analyze the encounter data to determine which healthcare expenditures, including co-insurance, co-payment or deductible payments, were paid out-of-pocket by patient 302, which healthcare expenditures were paid via a medical account, and which healthcare expenditures are eligible for payment via a medical account. As referred to herein, a medical account can refer to a Flexible Spending Account (FSA), a Health Savings Account (HSA), or any other tax-advantaged financial account intended for medical expenses. Such a determination can be made, for example, based on the encounter data (such as CPT codes). Based on this analysis, aggregator system 318 can distinguish between out-of-pocket healthcare expenditures and medical account expenditures to notify patient 302 (e.g., via the interactive GUI) how much they have paid out-of-pocket, how much they have paid using the medical account, and/or how much money remains in their medical account. Moreover, aggregator system 318 can identify healthcare expenditures that are eligible for payment via a medical account but were paid out of pocket, and can automatically generate an alert to patient 302 indicating a missed medical account eligible expense. In some cases, the alert can include a claim form generated by aggregator 318 to simplify the process of filing a claim for the medical account eligible expense.

Aggregator system 318 can also provide real-time spending alerts to patient 302 and/or other entities based on the encounter to catch accidental or fraudulent billing activities.

Furthermore, aggregator system 318 aggregate and anonymize encounter data across a plurality of patients to identify community health and/or healthcare spending trends. Aggregator system 318 can also use Optical Character Recognition (OCR) to parse, normalize, and store a patient-provided EOB for comparison against the encounter data.

Figure 4:
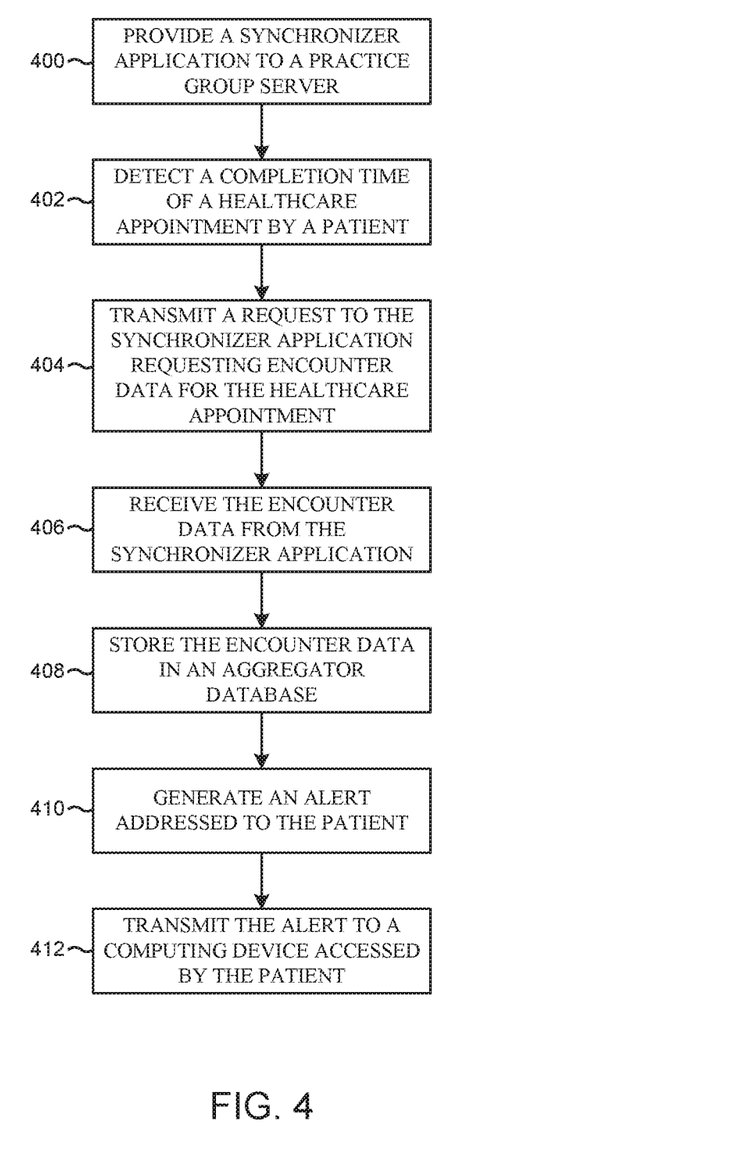
FIG. 4 illustrates an exemplary method embodiment.

Having disclosed some basic system components and concepts, the disclosure now turns to the exemplary method embodiment shown in FIG. 4. For the sake of clarity, the method is described in terms of a system 300, as shown in FIG. 3, configured to practice the method. The steps outlined herein are exemplary and can be implemented in any combination thereof, including combinations that exclude, add, or modify certain steps.

Referring to FIG. 4, the process begins at step 400 with an aggregator server (e.g., aggregator system 318) installing or otherwise providing a synchronizer application 320 to a practice group server 308. For instance, in some cases, aggregator server 318 can extend a synchronizer application 320 previously installed on practiced group server 308 to retrieve the encounter data. In other cases, aggregator system 318 can install or otherwise provide a synchronizer application 320 configured to retrieve the encounter data in addition to any existing sync infrastructure. Synchronizer application 320 can be configured to access a billing module 314 and/or data associated with practice group server 308 (e.g., by accessing an associated database, through one or more API-calls, etc.). Next, at step 402, aggregator server 318 detects a completion time of a healthcare appointment between a patient 302 and a provider 312 associated with practice group server 308. Aggregator server 318 can calculate the appointment completion time by, for example, using a known appointment start time and a known appointment duration.

Based on the completion time of the healthcare appointment, aggregator server 318 transmits a request for encounter data to synchronizer application 320 (step 404). Synchronizer application 320 then begins polling practice group server 308 (e.g., by accessing an associated database, through one or more API-calls, etc.) to retrieve the encounter data in response to the request. Synchronizer application 320 can continue polling practice group server 308 until the encounter data is retrieved or until a predetermined timeout occurs. Once retrieved, synchronizer application 320 transmits the encounter data to aggregator server 318 where it is received (step 406) and stored within an aggregator database (step 408). In some cases, such as those when the encounter data is encoded, aggregator server 318 can decode and normalize the encounter data prior to storing.

At step 410, aggregator server 318 generates an electronic alert addressed to a computing device accessible by patient 302 indicating an availability of encounter data for the healthcare appointment. Aggregator server 318 then transmits the alert to the computing device accessed by patient 302 (step 412). The alert is configured to cause the computing device to display the encounter data via an interactive user interface to enable patient 302 to review and/or dispute the encounter data.

Figure 5:
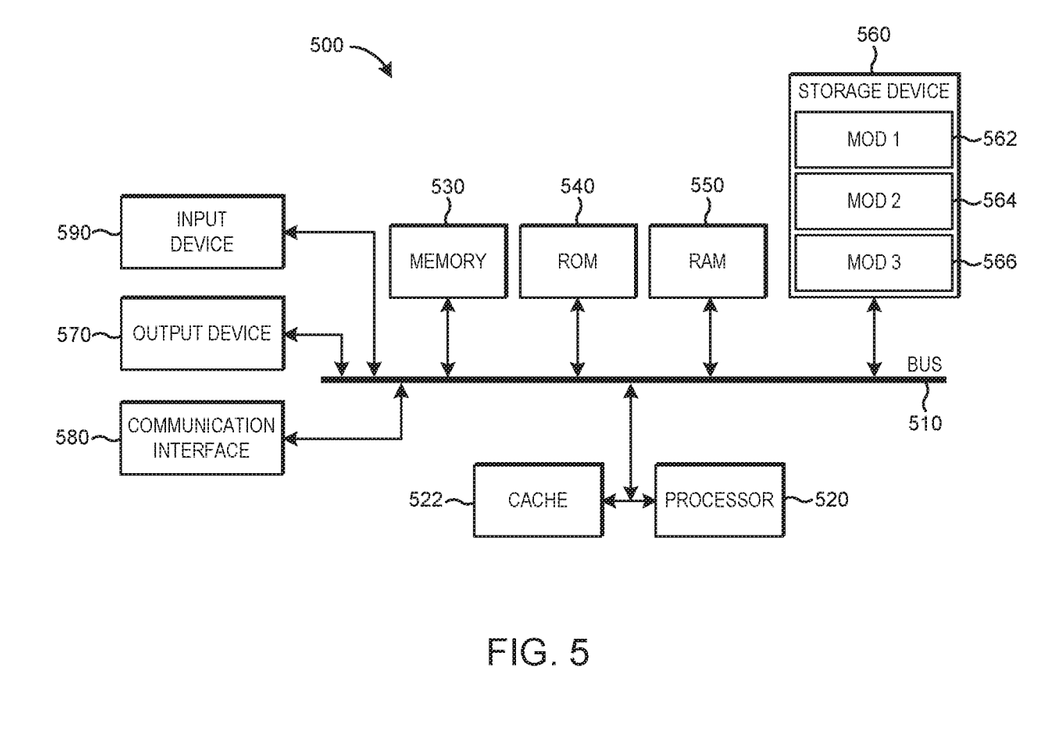
FIG. 5 illustrates a schematic diagram of exemplary computing systems for use with the present disclosure.

FIG. 5 illustrates a block diagram of a basic general purpose system or computing device which can be employed to practice the concepts, methods, and techniques disclosed herein. With reference to FIG. 5, an exemplary system and/or computing device 500 includes a processing unit (i.e., CPU or processor) 520 and a system bus 510 that couples various system components including the system memory 530 such as read only memory (ROM) 540 and random access memory (RAM) 550 to the processor 520. The system 500 can include a cache 522 of high-speed memory connected directly with, in close proximity to, or integrated as part of the processor 520. The system 500 copies data from the memory 530 and/or the storage device 560 to the cache 522 for quick access by the processor 520. In this way, the cache provides a performance boost that avoids processor 520 delays while waiting for data. These and other modules can control or be configured to control the processor 520 to perform various operations or actions. Other system memory 530 may be available for use as well. The memory 530 can include multiple different types of memory with different performance characteristics. It can be appreciated that the disclosure may operate on a computing device 500 with more than one processor 520 or on a group or cluster of computing devices networked together to provide greater processing capability. The processor 520 can include any general purpose processor and a hardware module or software module, such as module 1 562, module 2 564, and module 3 566 stored in storage device 560, configured to control the processor 520 as well as a special-purpose processor where software instructions are incorporated into the processor. The processor 520 may be a self-contained computing system, containing multiple cores or processors, a bus, memory controller, cache, etc. A multi-core processor may be symmetric or asymmetric. The processor 520 can include multiple processors, such as a system having multiple, physically separate processors in different sockets, or a system having multiple processor cores on a single physical chip. Similarly, the processor 520 can include multiple distributed processors located in multiple separate computing devices, but working together such as via a communications network. Multiple processors or processor cores can share resources such as memory 530 or the cache 522, or can operate using independent resources. The processor 520 can include one or more of a state machine, an application specific integrated circuit (ASIC), or a programmable gate array (PGA) including a field PGA.

The system bus 510 may be any of several types of bus structures including a memory bus or memory controller, a peripheral bus, and a local bus using any of a variety of bus architectures. A basic input/output (BIOS) stored in ROM 540 or the like, may provide the basic routine that helps to transfer information between elements within the computing device 500, such as during start-up. The computing device 500 may further include storage devices 560 or computer-readable storage media such as a hard disk drive, a magnetic disk drive, an optical disk drive, tape drive, solid-state drive, RAM drive, removable storage devices, a redundant array of inexpensive disks (RAID), hybrid storage device, or the like. The storage device 560 can include software modules 562, 564, 566 for controlling the processor 520. The system 500 can include other hardware or software modules. The storage device 560 is connected to the system bus 510 by a drive interface. The drives and the associated computer-readable storage devices provide nonvolatile storage of computer-readable instructions, data structures, program modules and other data for the computing device 500. In one aspect, a hardware module that performs a particular function includes the software component stored in a tangible computer-readable storage device in connection with the necessary hardware components, such as the processor 520, bus 510, display 570, and so forth, to carry out a particular function. In another aspect, the system can use a processor and computer-readable storage device to store instructions which, when executed by the processor, cause the processor to perform operations, a method or other specific actions. The basic components and appropriate variations can be modified depending on the type of device, such as whether the device 500 is a small, handheld computing device, a desktop computer, or a computer server. When the processor 520 executes instructions to perform "operations", the processor 520 can perform the operations directly and/or facilitate, direct, or cooperate with another device or component to perform the operations.

Although the exemplary embodiment(s) described herein employs the hard disk 560, other types of computer-readable storage devices which can store data that are accessible by a computer, such as magnetic cassettes, flash memory cards, digital versatile disks (DVDs), cartridges, random access memories (RAMs) 550, read only memory (ROM) 540, a cable containing a bit stream and the like, may also be used in the exemplary operating environment. Tangible computer-readable storage media, computer-readable storage devices, or computer-readable memory devices, expressly exclude media such as transitory waves, energy, carrier signals, electromagnetic waves, and signals per se.

To enable user interaction with the computing device 500, an input device 590 represents any number of input mechanisms, such as a microphone for speech, a touch-sensitive screen for gesture or graphical input, keyboard, mouse, motion input, speech and so forth. An output device 570 can also be one or more of a number of output mechanisms known to those of skill in the art. In some instances, multimodal systems enable a user to provide multiple types of input to communicate with the computing device 500. The communications interface 580 generally governs and manages the user input and system output. There is no restriction on operating on any particular hardware arrangement and therefore the basic hardware depicted may easily be substituted for improved hardware or firmware arrangements as they are developed.

For clarity of explanation, the illustrative system embodiment is presented as including individual functional blocks including functional blocks labeled as a "processor" or processor 520. The functions these blocks represent may be provided through the use of either shared or dedicated hardware, including, but not limited to, hardware capable of executing software and hardware, such as a processor 520, that is purpose-built to operate as an equivalent to software executing on a general purpose processor. For example the functions of one or more processors presented in FIG. 5 may be provided by a single shared processor or multiple processors. (Use of the term "processor" should not be construed to refer exclusively to hardware capable of executing software.) Illustrative embodiments may include microprocessor and/or digital signal processor (DSP) hardware, read-only memory (ROM) 540 for storing software performing the operations described below, and random access memory (RAM) 550 for storing results. Very large scale integration (VLSI) hardware embodiments, as well as custom VLSI circuitry in combination with a general purpose DSP circuit, may also be provided.

The logical operations of the various embodiments are implemented as: (1) a sequence of computer implemented steps, operations, or procedures running on a programmable circuit within a general use computer, (2) a sequence of computer implemented steps, operations, or procedures running on a specific-use programmable circuit; and/or (3) interconnected machine modules or program engines within the programmable circuits. The system 500 shown in FIG. 5 can practice all or part of the recited methods, can be a part of the recited systems, and/or can operate according to instructions in the recited tangible computer-readable storage devices. Such logical operations can be implemented as modules configured to control the processor 520 to perform particular functions according to the programming of the module. For example, FIG. 5 illustrates three modules Mod1 562, Mod2 564 and Mod3 566 which are modules configured to control the processor 520. These modules may be stored on the storage device 560 and loaded into RAM 550 or memory 530 at runtime or may be stored in other computer-readable memory locations.

One or more parts of the example computing device 500, up to and including the entire computing device 500, can be virtualized. For example, a virtual processor can be a software object that executes according to a particular instruction set, even when a physical processor of the same type as the virtual processor is unavailable. A virtualization layer or a virtual "host" can enable virtualized components of one or more different computing devices or device types by translating virtualized operations to actual operations. Ultimately however, virtualized hardware of every type is implemented or executed by some underlying physical hardware. Thus, a virtualization compute layer can operate on top of a physical compute layer. The virtualization compute layer can include one or more of a virtual machine, an overlay network, a hypervisor, virtual switching, and any other virtualization application.

The processor 520 can include all types of processors disclosed herein, including a virtual processor. However, when referring to a virtual processor, the processor 520 includes the software components associated with executing the virtual processor in a virtualization layer and underlying hardware necessary to execute the virtualization layer. The system 500 can include a physical or virtual processor 520 that receives instructions stored in a computer-readable storage device, which causes the processor 520 to perform certain operations. When referring to a virtual processor 520, the system also includes the underlying physical hardware executing the virtual processor 520.

Embodiments within the scope of the present disclosure may also include tangible and/or non-transitory computer-readable storage devices for carrying or having computer-executable instructions or data structures stored thereon. Such tangible computer-readable storage devices can be any available device that can be accessed by a general purpose or special purpose computer, including the functional design of any special purpose processor as described above. By way of example, and not limitation, such tangible computer-readable devices can include RAM, ROM, EEPROM, CD-ROM or other optical disk storage, magnetic disk storage or other magnetic storage devices, or any other device which can be used to carry or store desired program code in the form of computer-executable instructions, data structures, or processor chip design. When information or instructions are provided via a network or another communications connection (either hardwired, wireless, or combination thereof) to a computer, the computer properly views the connection as a computer-readable medium. Thus, any such connection is properly termed a computer-readable medium. Combinations of the above should also be included within the scope of the computer-readable storage devices.

Computer-executable instructions include, for example, instructions and data which cause a general purpose computer, special purpose computer, or special purpose processing device to perform a certain function or group of functions. Computer-executable instructions also include program modules that are executed by computers in stand-alone or network environments. Generally, program modules include routines, programs, components, data structures, objects, and the functions inherent in the design of special-purpose processors, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

Other embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Embodiments may also be practiced in distributed computing environments where tasks are performed by local and remote processing devices that are linked (either by hardwired links, wireless links, or by a combination thereof) through a communications network. In a distributed computing environment, program modules may be located in both local and remote memory storage devices.

The various embodiments described above are provided by way of illustration only and should not be construed to limit the scope of the disclosure. For example, the principles herein apply equally to optimization as well as general improvements. Various modifications and changes may be made to the principles described herein without following the example embodiments and applications illustrated and described herein, and without departing from the spirit and scope of the disclosure. Claim language reciting "at least one of" a set indicates that one member of the set or multiple members of the set satisfy the claim.

I claim:

1. A method, comprising: providing a synchronizer application installed on and configured to access data associated with a medical practice group server that lacks an application program interface to communicate with an aggregator server; receiving, by the aggregator server and from the synchronizer application, a start time and a duration of a healthcare appointment between a patient and a physician associated with the medical practice group server; determining, by the aggregator server, a completion time of the healthcare appointment based at least in part on the start time and the duration; based on the completion time, transmitting, by the aggregator server and to the synchronizer application, a request for encounter data for the healthcare appointment, wherein the synchronizer application is configured to poll the medical practice group server to retrieve the encounter data in response to the request, wherein the synchronizer application is configured to poll the medical practice group server until a predetermined timeout or the encounter data is retrieved; receiving, by the aggregator server and from the synchronizer application, the encounter data, wherein the encounter data includes one or more services rendered during the healthcare appointment; decoding and normalizing, by one of aggregator server and synchronizer application, prior to storing in the aggregator database, the encounter data that has been encoded using Current Procedural Terminology (CPT) codes; storing, by the aggregator server, the encounter data in an aggregator database; transmitting, in response to one of a communication from the aggregator server and a signal generated by the synchronizer based on the completion time, a billing request from the synchronizer application to a billing module on the medical practice group server; transmitting, in response to the billing request, encounter data from the billing module to one of an insurer and a clearing house for resolution; generating, by the aggregator server, an electronic alert addressed to a computing device accessible by the patient, the alert indicating an availability of encounter data for the healthcare appointment; transmitting, by the aggregator server, the alert to the computing device; receiving, by the aggregator server and from the computing device, an electronic response to the alert, wherein the response includes a request to access the encounter data for the healthcare appointment; and providing, by the aggregator server, an interactive user interface to the computing device, wherein the interactive user interface is configured to display the encounter data on the computing device.

2. The method of claim 1, wherein the request includes identifying information for the healthcare appointment, and wherein synchronizer application is further configured to match the healthcare appointment to the encounter data based on the request.

3. The method of claim 1, wherein the alert is one or more of an email, a Short Message Service (SMS), a Multimedia Messaging Service (MMS), a push notification, or an application launch.

4. The method of claim 1, further comprising: detecting, by the aggregator server, a delay or a rescheduling of the healthcare appointment; and recalculating, by the aggregator server, the completion time of the healthcare appointment based at least in part on the delay or the rescheduling.

5. The method of claim 1, further comprising: receiving, by the aggregator server, a booking request submitted via the interactive user interface, the booking request including at least an appointment time for a second healthcare appointment; and booking, by the aggregator server, the second healthcare appointment.

6. The method of claim 1, further comprising: receiving, by the aggregator server, a dispute message submitted via the interactive user interface, the dispute message identifying at least a portion of the encounter data being disputed; and transmitting, by the aggregator server and to the medical practice group server, the dispute message.

7. The method of claim 1, further comprising: identifying, by the aggregator server, a healthcare expenditure based at least in part on the encounter data; and categorizing, by the aggregator server, the healthcare expenditure as an out-of-pocket expenditure or a medical account eligible expenditure.

8. A system, comprising: a medical practice group server; and an aggregator server configured to: provide a synchronizer application installed on and configured to access data associated with the medical practice group server that lacks an application program interface to communicate with the aggregator server, the synchronizer application configured to receive a billing request from the aggregator server and in response communicate with a billing module on the medical practice group server to transmit encounter data to one of an insurer and a clearing house for resolution; receive from the synchronizer application a start time and a duration of a healthcare appointment between a patient and a physician associated with the medical practice group server; determine a completion time of the healthcare appointment based at least in part on the start time and the duration; based on the completion time, transmit, to the synchronizer application, one or more of the billing request and an encounter request for encounter data for the healthcare appointment, wherein the synchronizer application is configured to poll the medical practice group server to retrieve the encounter data in response to the encounter request, wherein the synchronizer application is configured to poll the medical practice group server until a predetermined timeout or the encounter data is retrieved; receive, from the synchronizer application, the encounter data, wherein the encounter data includes one or more services rendered during the healthcare appointment; decode and normalize, prior to storing in the aggregator database, the encounter data that has been encoded using Current Procedural Terminology (CPT) codes; store the encounter data in an aggregator database; generate an electronic alert addressed to a computing device accessible by the patient, the alert indicating an availability of encounter data for the healthcare appointment; transmit the alert to the computing device; receive, from the computing device, an electronic response to the alert, wherein the response includes a request to access the encounter data for the healthcare appointment; and provide an interactive user interface to the computing device, wherein the interactive user interface is configured to display the encounter data on the computing device.

9. The system of claim 8, wherein the request includes identifying information for the healthcare appointment, and wherein synchronizer application is further configured to match the healthcare appointment to the encounter data based on the request.

10. The system of claim 8, wherein the aggregator server is further configured to: receive a dispute message submitted via the interactive user interface, the dispute message identifying at least a portion of the encounter data being disputed; and transmit, to the medical practice group server, the dispute message.

11. The system of claim 8, wherein the alert is one or more of an email, a Short Message Service (SMS), a Multimedia Messaging Service (MMS), a push notification, or an application launch.

12. The system of claim 8, wherein the synchronizer application is configured to continuously poll the medical practice group server until the encounter data is retrieved or until a predetermined timeout occurs.

13. The system of claim 8, wherein the interactive user interface includes encounter data for one or more prior healthcare appointments by the patient.

14. A non-transitory computer-readable storage medium having stored therein instructions which, when executed by a processor, cause the processor to perform operations comprising: providing a synchronizer application installed on and configured to access data associated with a medical practice group server that lacks an application program interface to communicate with an aggregator server; receiving, by the aggregator server from the synchronizer application, a start time and a duration of a healthcare appointment between a patient and a physician associated with the medical practice group server; determining, by the aggregator server, a completion time of the healthcare appointment based at least in part on the start time and the duration; based on the completion time, transmitting, by the aggregator server and to the synchronizer application, a request for encounter data for the healthcare appointment, wherein the synchronizer application is configured to poll the medical practice group server to retrieve the encounter data in response to the request, wherein the synchronizer application is configured to poll the medical practice group server until a predetermined timeout or the encounter data is retrieved; receiving, by the aggregator server and from the synchronizer application, the encounter data, wherein the encounter data includes one or more services rendered during the healthcare appointment; decoding and normalizing, by one of aggregator server and synchronizer application, prior to storing in the aggregator database, the encounter data that has been encoded using Current Procedural Terminology (CPT) codes; storing, by the aggregator server, the encounter data in an aggregator database; transmitting, in response to one of a communication from the aggregator server and a signal generated by the synchronizer based on the completion time, a billing request from the synchronizer application to a billing module on the medical practice group server; transmitting, in response to the billing request, encounter data from the billing module to one of an insurer and a clearing house for resolution; generating, by the aggregator server, an electronic alert addressed to a computing device accessible by the patient, the alert indicating an availability of encounter data for the healthcare appointment; transmitting, by the aggregator server, the alert to the computing device; receiving, by the aggregator server and from the computing device, an electronic response to the alert, wherein the response includes a request to access the encounter data for the healthcare appointment; and providing, by the aggregator server, an interactive user interface to the computing device, wherein the interactive user interface is configured to display the encounter data on the computing device.

15. The non-transitory computer-readable storage medium of claim 14, wherein the request includes identifying information for the healthcare appointment, and wherein synchronizer application is further configured to match the healthcare appointment to the encounter data based on the request.

16. The non-transitory computer-readable storage medium of claim 14, wherein at least a portion of the encounter data is encoded, and wherein the aggregator server is configured to decode and normalize the encounter data prior to storing in the aggregator database.

17. The non-transitory computer-readable storage medium of claim 14, wherein the synchronizer application is configured to continuously poll the medical practice group server until the encounter data is retrieved or until a predetermined timeout occurs.

18. The non-transitory computer-readable storage medium of claim 14, having stored therein additional instructions which, when executed by the processor, cause the processor to perform operations comprising: receiving, by the aggregator server, a dispute message submitted via the interactive user interface, the dispute message identifying at least a portion of the encounter data being disputed; and transmitting, by the aggregator server and to the medical practice group server, the dispute message.

* * * * *